United States Patent [19]
Rolf

[11] Patent Number: 6,093,419
[45] Date of Patent: Jul. 25, 2000

[54] COMPLIANCE VERIFICATION METHOD AND DEVICE IN COMPULSORY DRUG ADMINISTRATION

[75] Inventor: David Rolf, Eden Prairie, Minn.

[73] Assignee: LecTec Corporation, Minnetonka, Minn.

[21] Appl. No.: 09/211,303

[22] Filed: Dec. 14, 1998

Related U.S. Application Data

[63] Continuation-in-part of application No. 08/483,717, Jun. 7, 1995, abandoned.

[51] Int. Cl.⁷ .............................. A61F 13/02; A61L 15/16; A61K 9/70
[52] U.S. Cl. ............................................. 424/448; 424/449
[58] Field of Search ...................................... 424/448, 449

[56] References Cited

U.S. PATENT DOCUMENTS

| | | | |
|---|---|---|---|
| 4,943,435 | 7/1990 | Baker et al. | 424/448 |
| 5,688,231 | 11/1997 | Flower | 604/20 |
| 5,846,974 | 12/1998 | Kallman et al. | 514/269 |

Primary Examiner—José G. Dees
Assistant Examiner—Kathryne E. Shelborne
Attorney, Agent, or Firm—Schwegman, Lundberg, Woessner & Kluth, P.A.

[57] ABSTRACT

A substance countering agent especially for an abused drug or alcohol or a contraceptive agent is contained in a flexible adherent sheet or patch used to achieve the transdermal delivery of the agent through the skin of a person. The patch is limp, fragile, and non-self-supporting. The patch has a weak structure and is sufficiently limp and fragile so that the patch cannot be removed from the skin and later reapplied to the skin as a smooth planar covering. A compliance verification method is also provided for compulsory drug administration. This novel method includes providing a flexible adhesive patch containing a substance countering agent to be administered transdermally to the patient and maintaining the patch sufficiently limp and fragile so that the patch cannot be removed from the skin and later reapplied to the skin as a smooth planar covering. Prior to being applied to the skin, a supporting sheet or carrier is provided for supporting the patch in an outstretched, wrinkle-free condition. The patch is applied to the skin and the supporting sheet or carrier is removed, leaving the patch on the skin as a thin, membranous covering.

29 Claims, 4 Drawing Sheets

COMPLIANCE VERIFICATION METHOD AND DEVICE IN COMPULSORY DRUG ADMINISTRATION

This is a continuation-in-part of a CPA application filed Aug. 27, 1998 which was in turn a continuation of application Ser. No. 08/483,717 filed Jun. 7, 1995, now abandoned.

FIELD OF THE INVENTION

This invention relates to a method and device for assuring compliance in the administration of pharmaceutical substances to a person.

BACKGROUND OF THE INVENTION

An array of pharmaceutical preparations have been used in treatment programs provided to addicts and others. This therapeutic interventional treatment can be termed a "pharmacologic treatment for addiction." Controlled substance blocking agents, also known as antagonist drugs, render illicit drugs ineffective by attenuating or blocking the effects of the substance. An antagonist is an agent that opposes or resists the action of an abused substance, tending to neutralize or impede its action. The action of an antagonist should provide motivation for the addict to cease abuse of the drug since he or she no longer feels its effects (while on the antagonist therapy). An aversive agent is a substance that when administered to a person acts to prevent drug abuse by inducing some negative effect when the illicit drug is ingested. The addict would be rendered incapacitated by becoming sick if the drug is ingested while undergoing aversive agent therapy. It is hoped that the addict will learn to modify his or her addictive behavior after repeated negative experience with the drug of abuse while on aversive agent therapy. A drug agonist is a substance that when administered to a person works by attenuating or eliminating the addict's craving for the abused drug. With no craving, the abused drug would not be used. This class of treatment compounds often express some abuse-drug-like effects and may have some abuse potential of their own. The present invention also concerns the mandatory administration of birth control drugs. The expression "pharmacologic treatment for addition" as used hereinbelow is intended to include all forms of therapeutic agents under the general heading "substance countering agents" including all of the above, namely, antagonists, agonists, and aversive agents. The expression "substance countering agents" also includes birth control drugs.

Courts sometimes make the therapeutic administration of an antagonist drug mandatory as a part of a sentence given to an alcohol or drug abuser for reducing dependence or use of controlled substances or alcohol. The most common of these are Methadone® (adanone hydrochloride) for heroin addiction or Antabuse® (disulfiram) for alcohol addiction. In other situations, certain individuals, e.g., mental patients, are required to take birth control drugs.

A major drawback of these pharmacologic treatment programs is that the patient or drug abuser all too often does not comply with its requirements, by failing to take the drug. Because transdermal patches can be removed easily from the skin, the applicant is not aware of a transdermal drug delivery patch ever having been used for the administration of antagonist drugs or other substance countering agents to drug or alcohol abusers. If the patch containing such a substance were applied to the skin, the patient could simply remove it immediately after leaving the hospital or probation center and then reapply it just before compliance was to be checked.

It is therefore one major object of the invention to find a way of assuring compliance with the mandatory administration of a substance countering agent to a person who may object to its use or simply forget to comply.

These and other more detailed and specific objects of the present invention will be better understood by reference to the following figures and detailed description which illustrate by way of example but a few of the various forms of the invention within the scope of the appended claims.

SUMMARY OF THE INVENTION

In one preferred form of the invention, a substance countering agent is contained in a flexible adherent sheet or patch used to achieve the transdermal delivery of the agent through the skin of a person. The term "substance countering agent" as used herein means any form of therapeutic agent for counteracting a substance taken by a person, including agonists, antagonists, and aversive agents and other substance counteracting agents including birth control agents. The patch is limp, fragile, and non-self-supporting. In summary, the patch has a weak structure and is sufficiently limp and fragile so that the patch cannot be removed from the skin and later reapplied to the skin as a smooth planar covering.

The invention also provides a compliance verification method for compulsory drug administration. This novel method comprises providing a flexible adhesive patch containing a substance countering agent to be administered transdermally to the patient and maintaining the patch sufficiently limp and fragile so that the patch cannot be removed from the skin and later reapplied to the skin as a smooth planar covering. Prior to being applied to the skin, a supporting sheet or carrier is provided for supporting the patch in an outstretched, wrinkle-free condition. The patch is applied to the skin and the supporting sheet or carrier is removed from the patch.

Additional features of the invention will be apparent from consideration of the accompanying specification, claims and drawings which illustrate by way of example but a few of the various ways in which the invention can be accomplished.

DETAILED DESCRIPTION OF THE INVENTION

The invention provides a compliance verification method and device to be used in the administration of substance countering agents for the control of drug and alcohol abuse and in the administration of birth control agents, or for any other agent where the compulsory administration of the agent has to be verified. The term "drug abuse" as used herein is intended to include alcohol abuse. The device comprises an easily applied, flexible transdermal delivery patch containing a substance countering agent. The patch is non-reappliable once removed and can be thought of as self-destructing so that anyone examining the patient or drug abuser can immediately tell that the patch had been removed or that an attempt has been made to reapply the patch after it has been removed, thereby assuring compliance by verifying that the patient is faithfully undergoing the required addiction therapy to help assure a speedy recovery.

The substance countering agent is contained in a flexible adherent sheet or patch used to achieve the transdermal delivery of the agent through the skin of a person. The patch is limp, fragile, and non-self-supporting, i.e., when an attempt is made to hold it upright, it droops of its own weight and tends to crumple into a wrinkled and formless heap. Because it has an adherent surface, portions of the patch stick together so that the crumpled patch is non-reappliable; i.e., it is virtually impossible to return it to its original form so that it can never be reapplied to the body as a smooth, wrinkle-free covering. In summary, the patch is constructed and arranged to have a weak structure and is sufficiently limp and fragile so that it cannot be removed from the skin and later reapplied to the skin as a smooth planar covering. The membranous non-self-supporting and adherent character of the patch allows various parts of the adhesive surface to touch one another with the adhesive forming strong cohesive bonds, especially along the margins and wherever wrinkles occur; in effect, adhering the patch to itself spontaneously in various places. This combination of touching and bonding to itself causes the patch to shrivel or crumple, especially along the edges, on its own accord, resulting in formless clumps. Because the patch bonds to itself spontaneously, the patch can be thought of as "self-agglomerating." After this happens, there is virtually no way that the patch can be returned to its original shape. The patch is therefore non-reappliable to the skin.

The invention also provides a compliance verification method for compulsory drug administration. This novel method comprises providing a flexible adhesive patch containing a substance countering agent to be administered transdermally to the patient and maintaining the patch sufficiently limp and fragile so that the patch cannot be removed from the skin and later reapplied to the skin as a smooth planar covering. Prior to being applied to the skin, a supporting sheet or carrier is provided in contact with the patch for supporting the patch in an outstretched, wrinkle-free condition. The patch is applied to the skin and the supporting sheet or carrier is removed from the patch.

The patch preferably includes a backing layer formed from plastic film and also has a tacky, i.e., pressure-sensitive, adhesive layer matrix formed from a coating of an adhesive material applied to at least one surface of the film backing. A preferred backing layer comprises relatively thin, non-self-supporting plastic film backing. The combined thickness of the backing film and the adhesive matrix coating is low enough to provide the requisite limp, non-self-supporting and self-agglomerating characteristics already mentioned causing the patch to bunch up once it becomes unsupported so that it cannot be returned to its original smooth, planar configuration that would allow it to be reapplied. The substance countering agent is dispersed in the adhesive layer matrix, but when it is soluble in the film backing, it can also be carried by the film.

Any well-known substance countering agent can be used including, but not limited to: disulfiram, carbimide, or DETC-Me for treating alcohol addiction; naloxone for treating opiate addiction; benzoylecgonine for treating cocaine addiction; Methadone® for treating heroin or morphine addiction; levonorgestrel as a contraceptive; buprenorphine as an opiate agonist for treating cocaine or opiate addiction; and naltrexone as an antagonist for treating opiate addiction. When used as a contraceptive, the contraceptive agent in the patch functions as a countering agent for hormonal substances present in the body which facilitate conception.

The thickness of the patch depends to a great extent upon the composition of the film and adhesive layer. If the chemical composition of the resin provides relatively limp film, e.g., polyvinylidine chloride (Saran®), it can be fairly thick, e.g., 2 mils ($50\mu$). However if a stiffer resin is used, e.g., polyester, then it should be thinner, e.g., 0.2 mils ($5\mu$). In all cases, the adhesive layer is also thin enough when considered together with the thickness of the film backing to provide characteristics that render the film non-reappliable as already described. A typical adhesive thickness is from about 0.1 mil to about 1.0 mil (about $2.5\mu$ to about $25\mu$). If the adhesive layer is supple and highly flexible, it can be thicker. But if the adhesive layer is strong and tough, it should be relatively thin, e.g, $5\mu$ to $25\mu$. In short, the combined thickness of the backing and adhesive layer cannot be so great as to interfere with the non-self-supporting and self-agglomerating characteristic of the patch which causes it to bunch up, shrivel, or to become crumpled when unsupported. Its agglomerated condition renders it non-reappliable to the skin. Consequently, the patient, parolee or other person who has been ordered to have the substance countering agent administered cannot cheat by removing and later reapplying the patch without being detected, thereby assuring compliance with the therapy program so as to hasten recovery.

In another embodiment of the invention, the patch is not removable from the skin but instead wears off over a period of time. The patch in this case comprises a paint-like or stain-like coating on the surface of the skin which is bonded to the skin but has little internal cohesive strength and thus cannot be peeled away from the skin but must wear off over time. The patch in this case can be made visible for inspection to make sure that it is in place and in operation in either of two ways: first, by making it visible with a dye or pigment or, second, by using a normally invisible fluorescent dye that fluoresces under a UV light. In both cases, an inspector can check to make sure the patch is in place and has not been removed prematurely, e.g., by washing it off.

The unique transdermal substance countering agent delivery system of the present invention is easy to apply and use. The patches of the present invention are supple, pliable, soft and will conform to the body contours when applied to the skin of the patient. They are non-irritating, have little or no odor, and are safe to use. They will stay reliably in place over extended periods of time, typically about two weeks, and will constantly supply the substance countering agent through the skin barrier to the patient for carrying out the rehabilitation therapy program that has been ordered. In addition, a person examining the patient can easily see whether the patch has been in use from the time it was first applied because, once removed, the patch is self-agglomerating and is consequently non-reappliable.

Figure 1:
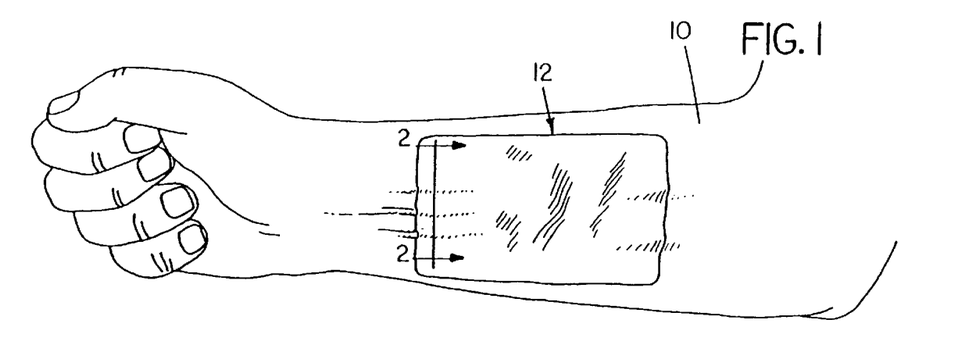
FIG. 1 is a perspective view showing a transdermal delivery patch for a substance countering agent shown applied to the skin of the forearm of a person.
Figure 2:
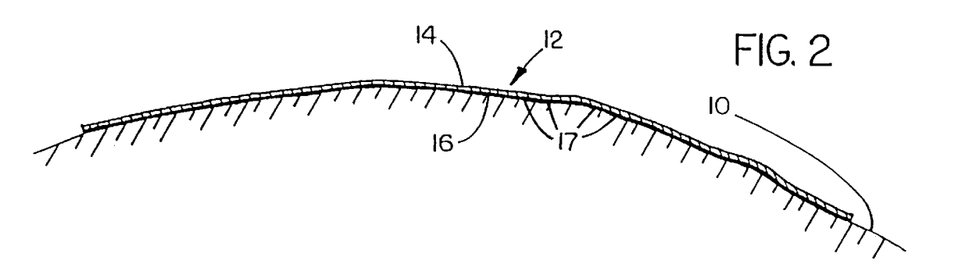
FIG. 2 is a greatly enlarged cross-sectional view taken along line 2—2 of FIG. 1.
Figure 3:
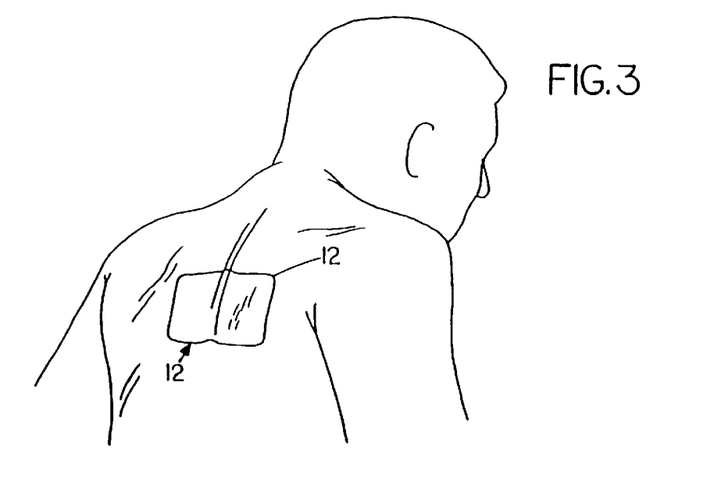
FIG. 3 is a perspective view showing the transdermal substance countering agent delivery patch applied to the back of a person.

Refer now to the figures. FIGS. 1–3 show a compliance verification device or patch 12 for the compulsory administration of a substance countering agent is applied to the forearm of a patient 10. The patch 12 which has a generally rectangular outline, in this case with rounded corners, includes a backing layer comprising a thin, flexible plastic film 14 and a pressure-sensitive adhesive layer as a matrix 16 in which is dispersed the substance countering agent 17. It will be seen, especially in FIG. 2, that the patch 12 is pliable and supple, conforming to the body contours of a patient. Typically, the patch appears on the skin as little more than a transparent membrane through which the skin can easily be seen. It need not, however, be transparent. The patch 12 is relatively weak, non-self-supporting, and sufficiently limp and fragile so that the patch cannot be removed from the skin of the patient 10 and later reapplied on the skin as a smooth planar covering. The backing layer in this case comprises a plastic film, e.g., 0.1 mil (2.5$\mu$) to 0.5 mil (12.5$\mu$) polyurethane plastic to which is applied a 0.5 mil (12.5$\mu$) matrix 16 of a pressure-sensitive adhesive containing 1.5 wt. % of a substance countering agent comprising an alcohol ingestion aversive agent comprising S-methyl-N,N-diethylthiocarbamate, herein referred to as "DETC-Me" (see U.S. Pat. No. 5,153,219). The thickness of the backing 14 can be increased depending upon its composition to, say, 2 mils or 3 mils provided, however, that the overall thickness of the patch 12 is such that the patch remains non-self-supporting so that the adhesive layer 16 bonds to itself causing formless clumps to convert the patch 12 to a self-agglomerated formless article that cannot be returned to its original shape. The structure of the patch 12 is maintained sufficiently fragile and limp that it is not self-supporting, so any attempt to remove the patch 12 from the skin will enable the patch 12 to become wrinkled and bond to itself in various places to form amorphous clumps. Consequently, once the patch 12 is removed, it cannot be returned to its original flat, planar configuration and reapplied to the skin as a smooth covering.

FIG. 3 illustrates a similar patch 12 applied to the back of a patient where it is out of the way and cannot be seen. In this position the patch 12 is located on a part of the body that will not be washed as vigorously as the hands and forearms, thereby reducing the chance for the patch to be removed prematurely through washing.

The outer layer of the skin, the stratum corneum, is made up of about 25 layers of epithelial cells totaling about 10$\mu$ thick. Consequently, the patch 12 is thinner than the skin barrier of the patient undergoing addiction therapy. The patient can be undergoing therapy for the abuse of any of a variety of controlled substances including cocaine, alcohol, heroin, barbiturates, and others. The invention is also useful in the administration of birth control materials of known composition. Because the patch 12 cannot be replaced on the skin when an attempt is made to do so without the shapeless remains clearly indicating that an attempt was made to reapply the patch, the invention overcomes a major shortcoming of previous therapy, for example pill dosage forms, by verifying compliance with the mandatory administration of the agent to the patient. The transdermal administration of the substance countering agent 17 will either render the abused drug ineffective or unattractive, and in that way will discourage or preclude the use of the addictive substance through any of various known mechanisms.

In a modified form of the invention, patch 12 is a paint-like or stain-like layer that is so thin, e.g., having a total thickness of less than 0.5 mil (12.5$\mu$), that it cannot be removed because the edge cannot be lifted and peeled back from the skin. The patch has little internal cohesive strength. If an attempt is made to remove it, e.g., by starting from one edge, no part of the patch can be lifted from the skin since the patch is adhered to the skin with a greater force than the internal strength of the patch 12. In this embodiment, the patch 12 can either be invisible to the unaided or made visible in one of two ways: first, with the use of a pigment or stain such as titanium dioxide or carbon black or can include a compound that will fluoresce under ultraviolet radiation so that the patch will be visible when the skin is inspected to make sure the patient has not removed the patch by washing. The backing of the patch 12 is essentially invisible except under ultraviolet light and erodes on the skin and sloughs off after a period of time, typically about two weeks. The backing 14 over the adhesive layer 16 acts as a protective covering and prevents the adhesive from picking up dirt.

In FIGS. 1–3, the backing 14 can comprise any of a variety of plastic resinous films including polyurethane, polyester, copolyester, ethylcellulose, cellulose acetate, carboxymethylcellulose, methylcellulose, polyvinylchloride, polyvinylpyrrolodine, polyethylene, polypropylene, polyvinylidene chloride, and other well known resins.

The pressure-sensitive adhesive layer 16 can be either a water miscible, i.e., hydrophilic, adhesive layer or a water immiscible, i.e., hydrophobic, adhesive which typically has a rubber base. It is preferred to apply the adhesive layer to the backing 14 as a liquid and dry it to form the finished coating 16. The adhesive layer can be applied as an aqueous dispersion, i.e., latex, e.g., by gravure roll or offset gravure coating. As the water is evaporated, the dispersed liquids and/or solids coalesce to form a continuous film. The pressure-sensitive adhesive layer 16 can be applied in a single pass or in more than one pass.

The invention also contemplates the application of the adhesive coating 16 as a liquid dissolved in an organic solvent. In this case, the pressure-sensitive adhesive layer, which is dissolved in an organic solvent, e.g., methyl ethyl ketone, is applied, e.g., by roll coating or spraying, after which the solvent is evaporated leaving the pressure-sensitive adhesive coating 16. This method of application is particularly useful for rubber-based hydrophobic adhesives.

If the adhesive is applied from an aqueous dispersion, the adhesive can comprise any of a variety of water dispersed adhesives including acrylate adhesives. The pressure-sensitive adhesive 16 can also comprise any of a variety of hydrophilic adhesive material such as those described in U.S. Pat. Nos. 4,675,009 and 4,307,117.

The substance countering agent 17 is dispersed in the adhesive layer 16 or in the backing 14 or both. Typically, the agent 17 is added to the adhesive composition before it is applied to the backing 14. The invention also contemplates placing a primary dose of the agent 17 in the adhesive 16 (a loading dose) and a secondary dose of the agent 17 in the film backing 14.

The thickness of the patch 12 depends upon the composition of the resin used in the film backing 14 and adhesive layer 16. If the backing 14 comprises polyurethane, a typical thickness range for the backing is from about 0.2 mil to about 1.0 mil (5$\mu$ to about 25$\mu$). The overall thickness of the patch 12 is, however, typically about 10$\mu$ to 150$\mu$ including the adhesive layer 16.

Figure 4:
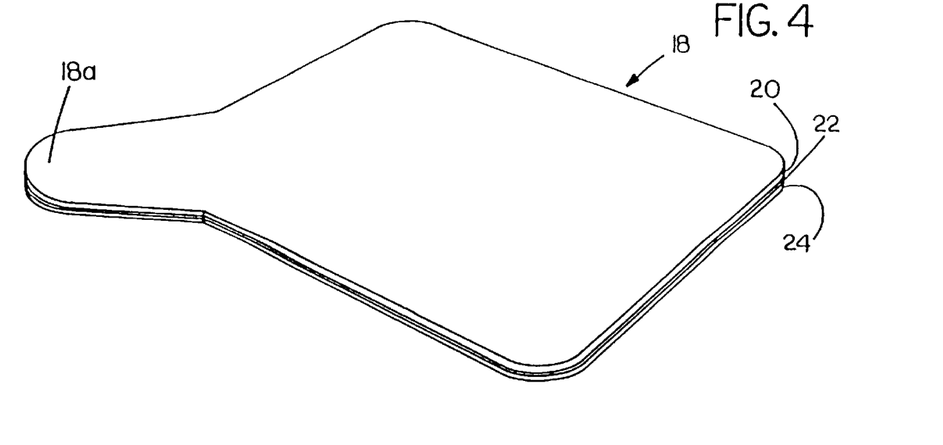
FIG. 4 is a perspective view of the patch before use with a release liner and carrier attached.
Figure 5:
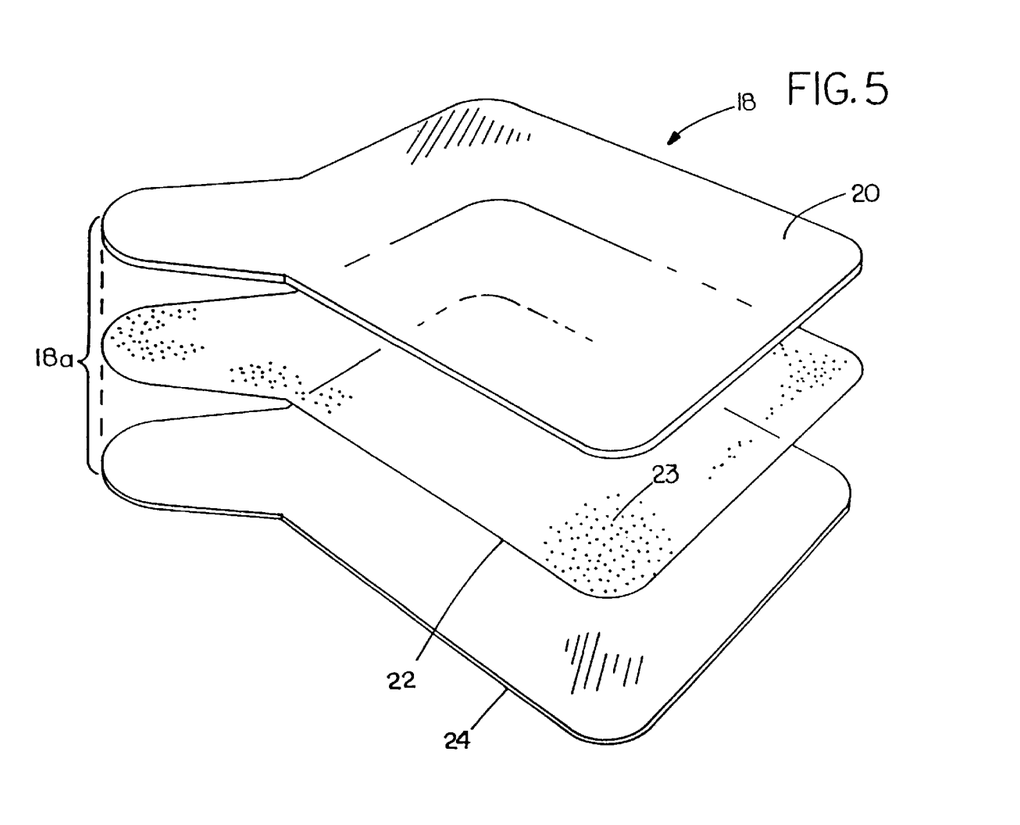
FIG. 5 is an exploded perspective view of the patch, the carrier and the release liner of FIG. 4 with the components separated for clarity of illustration.

Refer now to FIGS. 4 and 5 which illustrate another form of the invention as it appears before use. Shown in FIG. 4 is a patch assembly 18, in this case having a tab 18*a* in one corner to assist in applying the patch to the skin. The patch assembly 18 includes a removable release liner 20 such as a 5 mil layer of polyethylene. To the release liner 20 is attached a patch 22 which in this instance comprises a 0.5 mil layer of polyurethane to which is applied a $1\mu$ to $50\mu$ thick layer of adhesive 23 containing an antagonist comprising DETC-Me in the amount of 5% by weight. All quantities herein are expressed either in parts or percent by weight as indicated. To the lower surface of the patch 22 as seen in the figures is applied a carrier film 24 comprising a 2 mil layer of bi-axially oriented polypropylene (BOPP). The patch 22 is held against the carrier film 24 by weak electrostatic forces or Van Der Waals forces known as "static cling." Refer now to FIGS. 6–12 which illustrate the application and use of the patch.

Figure 6:
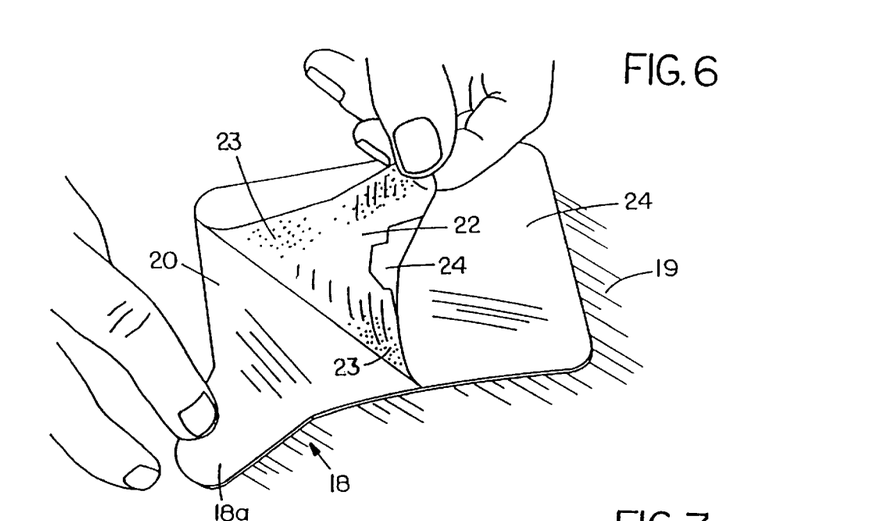
FIG. 6 is a perspective view showing the patch and carrier being removed from the release liner.

As shown in FIG. 6, the patch assembly 18 is placed before use on a surface such as a tabletop 19. The patch 22 and the carrier film 24 are then removed simultaneously from the release liner 20 as a single unit by peeling them back manually as shown in the figure. The liner 20 is then disposed of.

Figure 7:
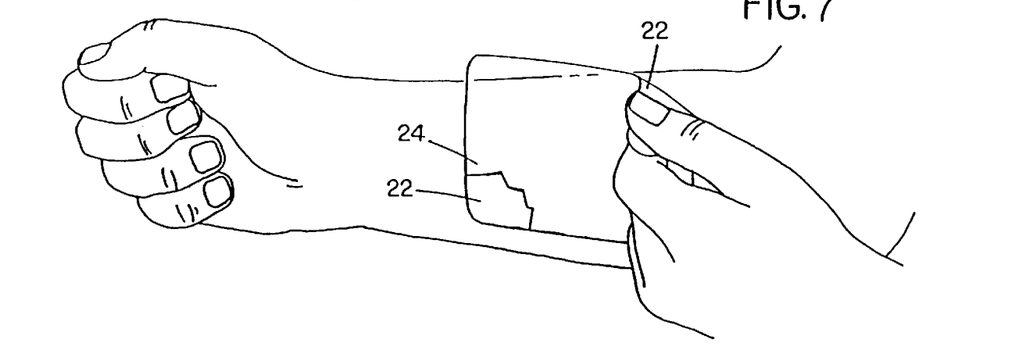
FIG. 7 is a perspective view showing a patch as it is applied to the skin while supported by the carrier film.

FIG. 7 illustrates the application of the patch 22 to the skin while the patch 22 is still supported by the carrier film 24. The adhesive 23 covering the lower surface of the patch 22 will securely bond the patch 22 to the skin of the patient. The adhesive layer 23 also contains the substance countering agent already described.

Figure 8:
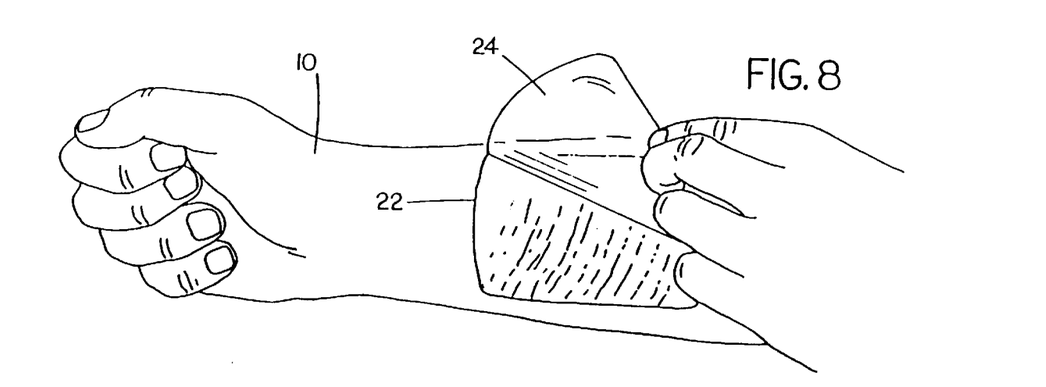
FIG. 8 is a perspective view showing removal of the carrier film from the applied patch.
Figure 9:
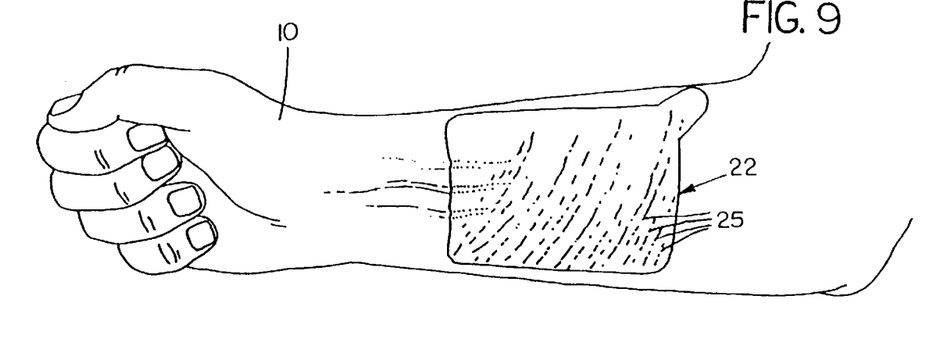
FIG. 9 is a perspective view of the patch as it appears on the skin of a patient during use.

In FIG. 8 the application of the patch 22 is completed by manually removing the carrier film 24 from the back of the patch 22. The patch 22 now is securely bonded to the skin as a thin and usually, but not necessarily, transparent membranous layer as shown in FIG. 9. The patch 22 is thin enough so that wrinkles 25 appear in the patch 22 where the skin is wrinkled. In this condition the patch 22 will remain on the skin of the person 10 while the substance countering agent within the patch is slowly absorbed through the stratum corneum into the blood of the patient, thereby either preventing or interfering with the use of the controlled substance by the patient or providing a birth control function.

Figures 10, 11:
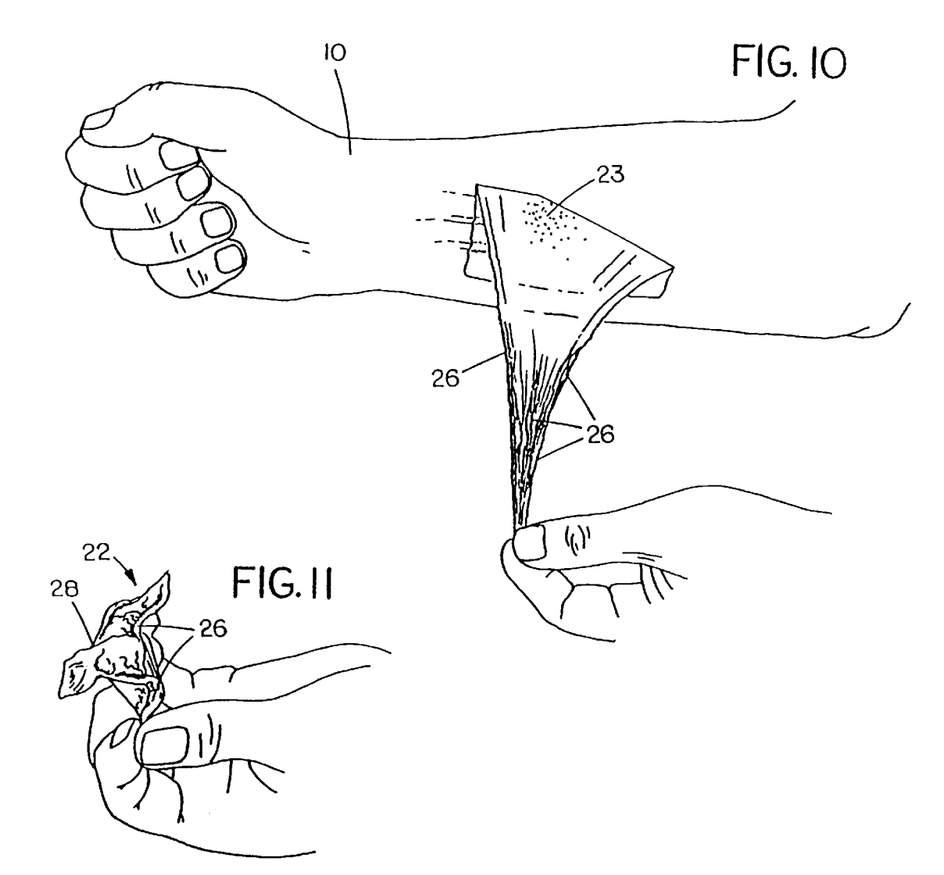
FIG. 10 is a perspective view showing an attempt to remove the patch from the skin of the forearm.
FIG. 11 shows a perspective view of the patch as it appears after it has been removed.

FIGS. 10 shows an attempt made by the person to remove the patch 22. It will be seen that as the patch 22 is being removed, wrinkles are already beginning to form along the edges of the patch. As this happens, the adhesive 23 causes various portions of the patch 22 that come in contact to become bonded together, especially at the margins or wherever wrinkles occur, in effect, adhering the patch to itself spontaneously. Because of this self-agglomerating character of the patch 22, the patch will crumple or shrivel of its own accord, resulting in formless clumps 26 which result in an amorphous mass that can never be returned to its original planar form and reapplied as a smooth, wrinkle-free coating to the skin. This will, consequently, prevent an addict or other person using the invention from cheating by removing the patch 22 shortly after it is applied and then attempting to reapply it just before being reexamined, thereby assuring compliance with the addiction therapy program prescribed for the patient and helping to assure a prompt recovery.

FIG. 11 shows the patch 22 after removal with the clumps of agglomerate material 26 that shrivel the patch 22 and reduce it to a formless agglomerated mass 28.

Typical substance countering agents and their activity are illustrated in the following table.

| Some Pharmacologic Treatments for Addiction and the Drugs Upon Which They Operate | | |
|---|---|---|
| Aversive Agent | Drug Operated Upon | Result |
| Antabuse ® (disulfiram) | Ethanol | Nausea |
| DETC-Me(S-methyl-N, N-diethyl thiocarbamate) | Ethanol | Nausea |
| Temposil (carbimide, cyanamide) | Ethanol | Nausea |
| Antagonist | Drug Operated Upon | Result |
| Naloxone | Opiates | Blocks Effects |
| Naltrexone | Opiates | Blocks Effects |
| Buprenorphine | Opiates, Stimulants | Blocks Some Effects |
| Fluphenazine | Cocaine, Amphetamines | Blocks Effects |
| Agonist | Drug Operated Upon | Result |
| Methadone ® | Heroin, Morphine | Reduces Craving |
| Benzoylecgonine | Cocaine | Reduces Craving? |
| Buprenorphine | Opiates | Reduces Craving? |
| Fentanyl | Opiates | Reduces Craving? |
| Bromocryptine | Cocaine, Amphetamines | Reduces Craving |

? indicates our current understanding

The invention will be better understood by reference to the following examples which illustrate typical formulations for the adhesive layer 16 and 23.

| % | | % range |
|---|---|---|
| | Example 1 | |
| 32 | Glycerin | 30–40 |
| 21 | Propylene Glycol | 10–30 |
| 1.5 | DETC-ME | 1–10 |
| 25 | Karaya | 20–30 |
| 20.5 | B. F. Goodrich 26171 | 15–30 |
| 100% | | |
| | Example 2 | |
| 5 | Isopropyl Myristate | 1–10 |
| 5 | DETC-Me | 1–20 |
| 40 | B. F. Goodrich 26171 | 10–70 |
| 45 | B. F. Goodrich 26222 | 10–70 |
| 100% | | |
| | Example 3 | |
| 20 | Karaya | 20–25 |
| 35 | Glycerin | 30–40 |
| 10 | Propylene Glycol | 5–15 |
| 14 | B. F. Goodrich 26145 | 10–20 |
| 14 | B. F. Goodrich 26222 | 10–20 |
| 7 | Benzoylecgonine | 5–25 |
| 100% | | |
| | Example 4 | |
| 30 | Glycerin | 25–35 |
| 12 | Karaya | 10–25 |
| 5 | Lodex | 1–10 |
| 9 | 34X | 1–15 |
| 20 | Propylene Glycol | 10–25 |

-continued

| % | | % range |
|---|---|---|
| 15 | Flexacryl 1615 | 10–25 |
| 9 | Methadone | 5–25 |
| 100% | | |

Example 5

| % | | % range |
|---|---|---|
| 45 | B. F. Goodrich 26171 | 10–70 |
| 45 | B. F. Goodrich 26415 | 10–70 |
| 5 | Levonorgestrel | 1–25 |
| 5 | Miglyol 818 | 1–20 |
| 100% | | |

Example 6

| % | | % range |
|---|---|---|
| 40 | B. F. Goodrich 26171 | 10–70 |
| 40 | B. F. Goodrich 26222 | 10–70 |
| 5 | Propylene Glycol | 1–10 |
| 10 | Buprenorphine | 1–30 |
| 5 | Miglyol 812 | 1–10 |
| 100% | | |

Example 7

| % | | % range |
|---|---|---|
| 20 | Karaya | 0–25 |
| 30 | Glycerin | 0–40 |
| 10 | Propylene Glycol | 5–30 |
| 5 | Isopropyl Myristate | 0–20 |
| 15 | B. F. Goodrich 26171 | 10–80 |
| 15 | B. F. Goodrich 26222 | 10–80 |
| 5 | Naltrexone | 1–25 |
| 100% | | |

Footnotes:

DETC-ME is an alcohol ingestion aversive agent. It is the active metabolite of disulfiram—Faiman U.S. Pat. No. 5,153,219

B. F. Goodrich 26171, 26222, 26415 are acrylic ester copolymer emulsion adhesives made by B.F. Goodrich of Brecksville, Ohio Isopropyl myristate is a lipophilic solubilizer which perhaps acts as an absorption enhancer.

Benzoylecgonine is thought to be useful in treating cocaine addiction. Its mode of action may be as an antagonist or agonist or both.

Methadone® is a compound used in treating heroin or morphine (opiate) addiction. It is thought to be an antagonist and an agonist.

Levonorgestrel is a synthetic hormone progestin which is the active ingredient in Norplant contraceptive.

Miglyol 812, 818 are lipophilic esters useful as solubilizing agents and possibly absorption enhancers.

Buprenorphine is an opiate antagonist which is thought to be useful in treating cocaine addiction or opiate addiction.

Naltrexone is an opiate antagonist which blocks the effects of addictive opiate drugs.

All these adhesive formulations are mixed uniformly in a suitable mixer, e.g., a high speed multi-bladed mixer or roller type mixer such as a Lightening™ mixer and coated as a layer about 2 mil (50μ) thick onto thin (½ mil) film plastics such as polyurethane, Saran®), copyester, PVDC. The adhesive can be applied by knife over roll coating or by gravure coating. The film is supported with a disposable carrier film 24 and the adhesive side is covered with release liner 20.

Polyurethane film and copolyester film are available from Flexcon Company, Spencer, Mass. These films arc also available from Courtaulds Performance Film, Chandler, Ariz.

Saran® is a polyvinylidene chloride (PVCD) film available from Dow Chemical, Midland, Mich.

Ethyl cellulose is available from FMC Corporation, Philadelphia, Pa.

The following example illustrates the use of the invention for mandatory birth control.

Example 8

| % | | % range |
|---|---|---|
| 80 | Ethyl cellulose | 60–90* |
| 10 | Propylene Glycol | 5–20* |
| 5 | Levonorgestrel | 1–20* |
| 5 | Miglyol 812 | 0–20* |
| 100% | | |

*The composition of Example 8 provides an extremely thin, paint-like elastic backing which would be invisible and non-removable. It simply erodes from the skin.

The formulation of Example 8 is mixed and coated as a liquid onto a removable carrier film 24. Once the film 22 (5μ to 100μ thick) containing the birth control drug has been cast on the carrier film 24 and dried, the thin film can be coated by spray coating, reverse gravure coating, etc. with a suitable adhesive 23 (B.F. Goodrich 26171, etc.) and dried. The adhesive 23 is then covered with a release liner 20. If desired, the adhesive 23 is the alternative pre-loaded with the drug described in the formula shown in Example 5.

The applicant's patches are opioid-free so that instead of administering more of an opioid to which a user may be addicted, they contain a substance-countering agent that acts to nullify or discourage the use of opioids by an addict. It should also be noted that the applicant's patch is devoid of a barrier such that the substance-countering agent is free to be delivered transdermally to the patient while the patch is bonded to the skin.

Many variations of the present invention within the scope of the appended claims will be apparent to those skilled in the art once the principles described herein are understood.

What is claimed is:

1. A patch suitable for transdermal drug administration through the skin of a person comprising:

a plastic film having two sides, an adhesive layer coated on one side of the plastic film, and a drug contained in the adhesive layer, wherein the plastic film and adhesive layer of the patch are of a combined thickness, flexibility and adhesiveness that the patch is structurally non-self-supporting and is self agglomerating, and wherein the adhesive layer is capable of releasing the drug upon contact of the adhesive layer and the skin of the person.

2. A patch according to claim 1 wherein the drug is a substance countering agent.

3. A patch according to claim 2 wherein the substance countering agent is selected from the group consisting of an alcohol aversive agent, an opiate antagonist agent, a cocaine agonist, a barbiturate antagonist, an amphetamine antagonist, and a birth control composition.

4. A patch according to claim 2 wherein the substance countering agent is selected from the group consisting of disulfiram, carimide, cyanamide, fentanyl, addenone hydrochloride, DETC-Me, benzoylecgonine, buprenorphine, levonorgestrel, naltrexone, naloxone, fluphenazine and bromocryptine.

5. A method for the administration of a drug through the skin of a person comprising:

providing a non-self-supporting patch comprising a plastic film having two sides, an adhesive layer which contains the drug and which is coated on one side of the plastic film, and a second support sheet contacting the side of the film opposite the adhesive layer, wherein the plastic film and adhesive layer of the patch are of a combined thickness, flexibility and adhesiveness that the patch without the second support sheet is structurally non-self-supporting and is self agglomerating, and wherein the adhesive layer is capable of releasing the drug upon contact of the adhesive layer and the skin of the person, applying the patch to the skin of a patient so that the adhesive layer contacts the skin, and removing the second support sheet from the patch.

6. A method according to claim 5 wherein the drug is a substance countering agent and is selected from the group consisting of an alcohol aversive agent, an opiate antagonist agent, a cocaine agonist, a barbiturate antagonist, an amphetamine antagonist, and a birth control composition.

7. A method according to claim 6 wherein the substance countering agent is selected from the group consisting of disulfiram, carbimide, cyanamide, fentanyl, addenone hydrochloride, DETC-Me, benzoylecgonine, buprenorphine, levonorgestrel, naltrexone, naloxone, fluphenazine and bromocryptine.

8. A method according to claim 5 wherein the adhesive layer comprises a pressure-sensitive adhesive matrix.

9. A patch according to claim 1 wherein the plastic film is formed from a plastic resin, and the adhesive layer is a pressure-sensitive adhesive matrix applied as a hydrophilic fluid coating and solidified.

10. A patch according to claim 1 wherein the adhesive layer is a matrix comprising a hydrocolloidal dispersion-forming hydrophilic polymer and the drug is dispersed in the matrix.

11. A patch according to claim 10 wherein the hydrophilic polymer is a polysaccharide polymer and an emulsion adhesive is dispersed in the matrix.

12. A patch according to claim 11 wherein the polysaccharide polymer is karaya.

13. A patch according to claim 11 wherein the matrix comprises about 10–30 parts by weight of the hydrophilic polysaccharide polymer, about 0–70 parts by weight of a polyhydric alcohol, and about 0–70 parts by weight of an emulsion adhesive.

14. A patch according to claim 13 wherein the polysaccharide polymer is karaya.

15. A patch according to claim 13 wherein the polyhydric alcohol is glycerin or propylene glycol.

16. A patch according to claim 13 wherein the emulsion adhesive is an acrylic ester copolymer adhesive.

17. A patch according to claim 1 wherein the plastic film comprises a paint-like elastic backing film which is non-removable from the skin except by eroding from the skin, and the adhesive layer is a pressure-sensitive adhesive matrix which is coated onto the backing film.

18. A patch according to claim 17 wherein the paint-like elastic backing film comprises an admixture of a film-forming polymer and a polyhydric alcohol.

19. A patch according to claim 18 wherein the drug is dispersed in the adhesive layer.

20. A patch according to claim 19 wherein the drug is a birth control drug.

21. The patch according to claim 20 wherein the birth control drug is levonorgestrel.

22. A patch suitable for transdermal drug administration through the skin of a person comprising, a) a backing layer that is non-removable from the skin except by eroding from the skin, the backing layer comprising a polymeric film, b) a pressure-sensitive adhesive matrix coated and solidified on at least one side of the backing layer, c) the drug contained in the backing layer, and wherein the backing layer and adhesive matrix are of a combined thickness, flexibility and adhesiveness that the patch is structurally non-self-supporting and is self agglomerating, and wherein the adhesive matrix is capable of releasing the drug upon contact of the adhesive layer and the skin of the person.

23. A patch according to claim 22 wherein the drug is selected from the group consisting of disulfiram, carbimide, cyanamide, fentanyl, addenone hydrochloride, DETC-Me, benzoylecgonine, buprenorphine, levonorgestrel, naltrexone, naloxone, fluphenazine and bromocryptine.

24. A patch according to claim 1 further comprising a second support sheet contacting the side of the plastic film opposite the adhesive layer.

25. A patch according to claim 24 further comprising a removable release liner contacting the adhesive layer so that the adhesive layer is between the removable release liner and the flexible plastic film.

26. A patch according to claim 1 wherein the combined thickness of the flexible plastic film and the adhesive layer is in the range of from about 6 to about 150 microns.

27. A patch according to claim 1 wherein the thickness of the flexible plastic film is from about 5 to about 100 microns.

28. A patch according to claim 1 wherein the thickness of the adhesive layer is from about 1 to about 50 microns.

29. A method according to claim 7 further comprising providing in the providing step a patch with a removable release liner contacting the adhesive layer so that the adhesive layer is between the removable release liner and the plastic film, and before the applying step, removing the removable release liner from the patch.

* * * * *

UNITED STATES PATENT AND TRADEMARK OFFICE
CERTIFICATE OF CORRECTION

PATENT NO. : 6,093,419

DATED: July 25, 2000

INVENTOR(S): Rolf

It is certified that error appears in the above-identified patent and that said Letters Patent is hereby corrected as shown below:

In claim 1, column 10, line 52, delete "as is", therefor.

In claim 1, column 10, line 52, delete "self agglomerating," and insert --, self agglomerating, sufficiently limp and fragile so that the patch cannot be removed from the skin and later reapplied on the skin as a smooth planar covering,--, therefor.

In claim 5, column 11, line 11, delete "as is", therefor.

In claim 5, column 11, line 11, delete "self agglomerating" and insert --, self agglomerating, sufficiently limp and fragile so that the patch cannot be removed from the skin and later reapplied on the skin as a smooth planar covering,--, therefor.

In claim 22, column 12, line 25, delete "as is", therefor.

In claim 22, column 12, line 25, delete "self agglomerating" and insert --, self agglomerating, sufficiently limp and fragile so that the patch cannot be removed from the skin and later reapplied on the skin as a smooth planar covering,--, therefor.

UNITED STATES PATENT AND TRADEMARK OFFICE
CERTIFICATE OF CORRECTION

PATENT NO. : 6,093,419
DATED : July 25, 2000
INVENTOR(S) : Rolf

It is certified that error appears in the above-identified patent and that said Letters Patent is hereby corrected as shown below:

In claim 22, column 12, line 26, delete "matrix" and insert --layer--, therefor.

In claim 29, column 12, line 48, delete "claim 7" and insert --claim 5--, therefor.

Signed and Sealed this

First Day of May, 2001

Attest:

NICHOLAS P. GODICI

Attesting Officer

Acting Director of the United States Patent and Trademark Office